(12) United States Patent
Lam

(10) Patent No.: US 9,402,976 B2
(45) Date of Patent: Aug. 2, 2016

(54) TRI-CURVE ELONGATE MEDICAL DEVICE

(71) Applicant: St. Jude Medical, Atrial Fibrillation Division, Inc., St. Paul, MN (US)

(72) Inventor: Lindsay Lam, Costa Mesa, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 122 days.

(21) Appl. No.: 13/796,701

(22) Filed: Mar. 12, 2013

(65) Prior Publication Data

US 2014/0276645 A1 Sep. 18, 2014

(51) Int. Cl.
*A61M 25/092* (2006.01)
*A61M 25/01* (2006.01)
*A61B 18/14* (2006.01)
*A61B 5/06* (2006.01)
*A61B 18/00* (2006.01)

(52) U.S. Cl.
CPC ........ *A61M 25/0105* (2013.01); *A61B 18/1492* (2013.01); *A61M 25/0136* (2013.01); *A61M 25/0147* (2013.01); *A61B 5/068* (2013.01); *A61B 2018/00797* (2013.01); *A61B 2018/00821* (2013.01)

(58) Field of Classification Search
CPC .................. A61M 2025/015; A61M 25/0105; A61M 25/0147; A61M 25/0133–25/0144
USPC .................. 604/528, 529, 533, 534
See application file for complete search history.

(56) References Cited

U.S. PATENT DOCUMENTS

| 5,358,478 | A | * | 10/1994 | Thompson et al. ........ 604/95.04 |
| 5,472,017 | A | * | 12/1995 | Kovalcheck .................. 138/103 |
| 5,480,382 | A | * | 1/1996 | Hammerslag et al. ........ 604/528 |
| 6,233,476 | B1 | | 5/2001 | Strommer et al. |
| 6,690,963 | B2 | | 2/2004 | Ben-Haim et al. |
| 7,197,354 | B2 | | 3/2007 | Sobe |
| 7,263,397 | B2 | | 8/2007 | Hauck et al. |
| 7,386,339 | B2 | | 6/2008 | Strommer et al. |
| 7,848,789 | B2 | | 12/2010 | Govari et al. |
| 8,123,721 | B2 | | 2/2012 | Tegg |
| 2007/0270679 | A1 | | 11/2007 | Nguyen et al. |
| 2012/0203169 | A1 | | 8/2012 | Tegg |

OTHER PUBLICATIONS

International Search Report and Written Opinion in PCT application No. PCT/US2014/023200 Jul. 21, 2014.

* cited by examiner

*Primary Examiner* — Aarti B Berdichevsky
(74) *Attorney, Agent, or Firm* — Dykema Gossett PLLC

(57) ABSTRACT

An embodiment of an elongate medical device may comprise a shaft body having a distal end portion and a proximal end portion and three or more deflection wire assemblies, each deflection wire assembly comprising a flat wire coupled to the distal end portion and configured to deflect the distal end portion. Each flat wire may have a respective length defining a respective deflection radius, wherein each deflection radius is different.

13 Claims, 10 Drawing Sheets

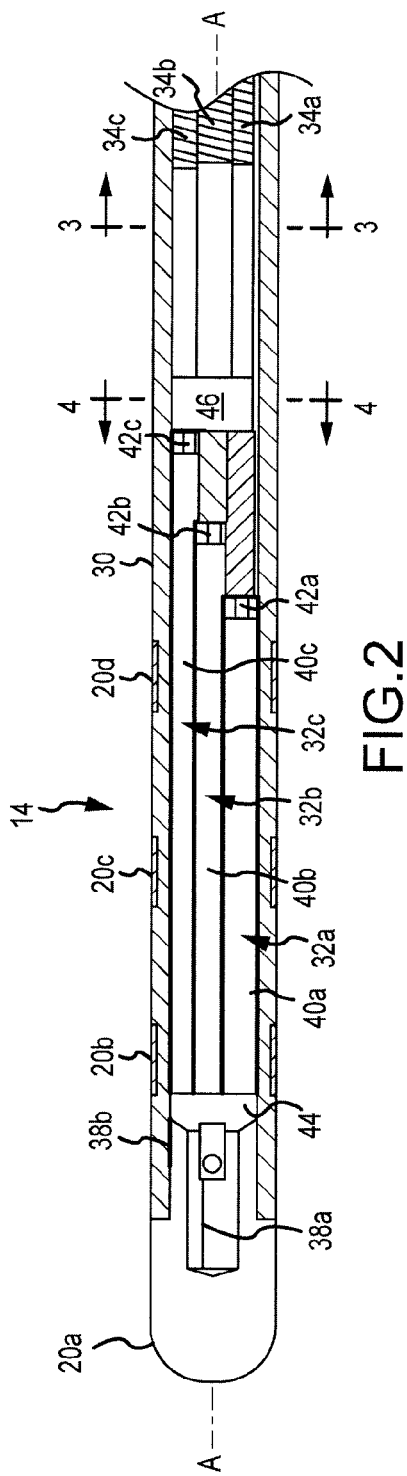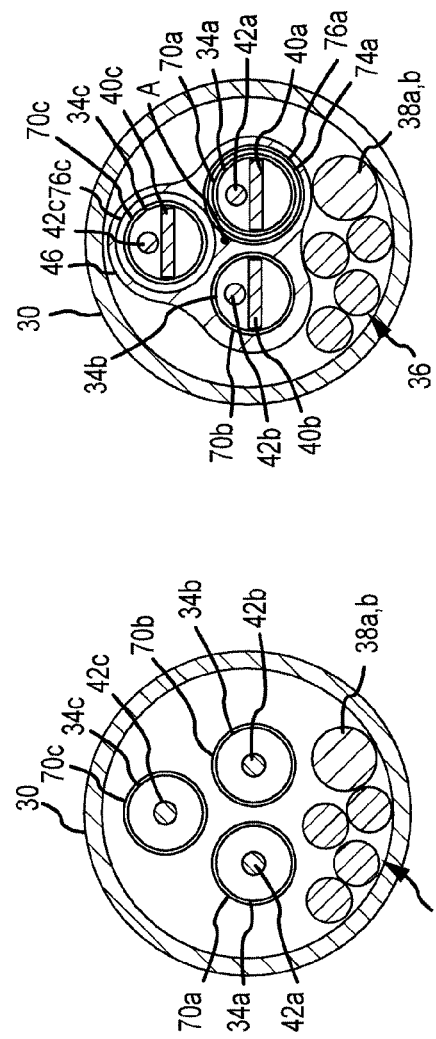

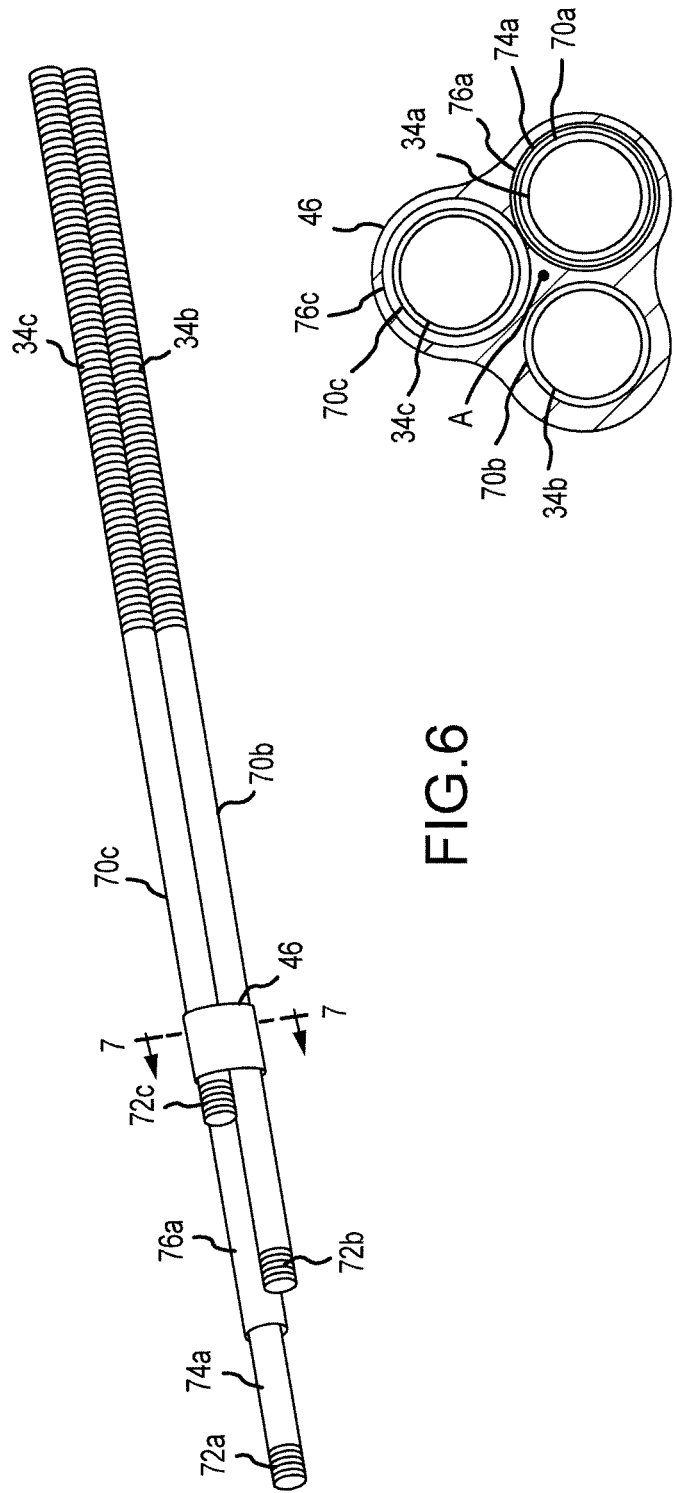

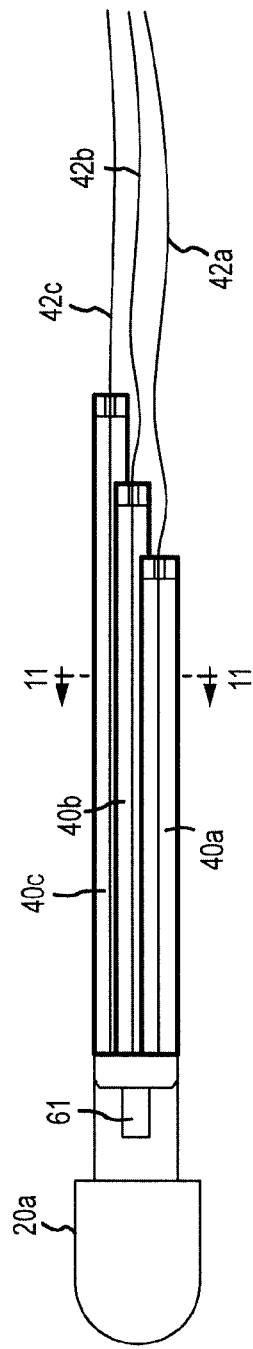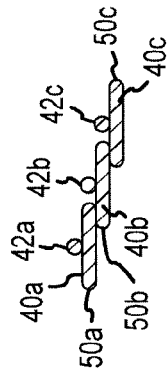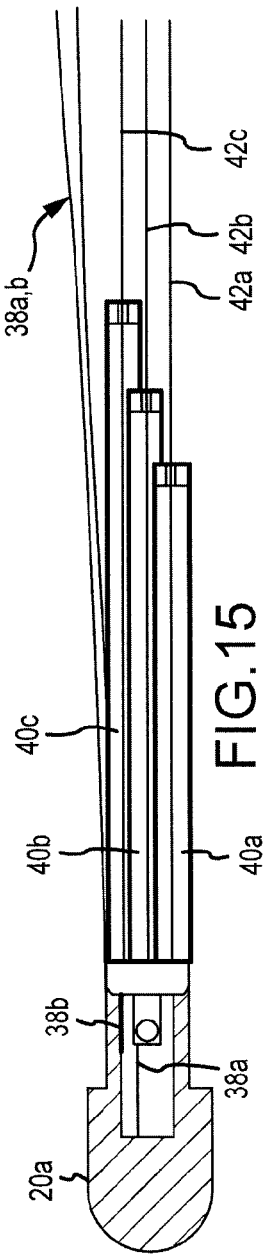

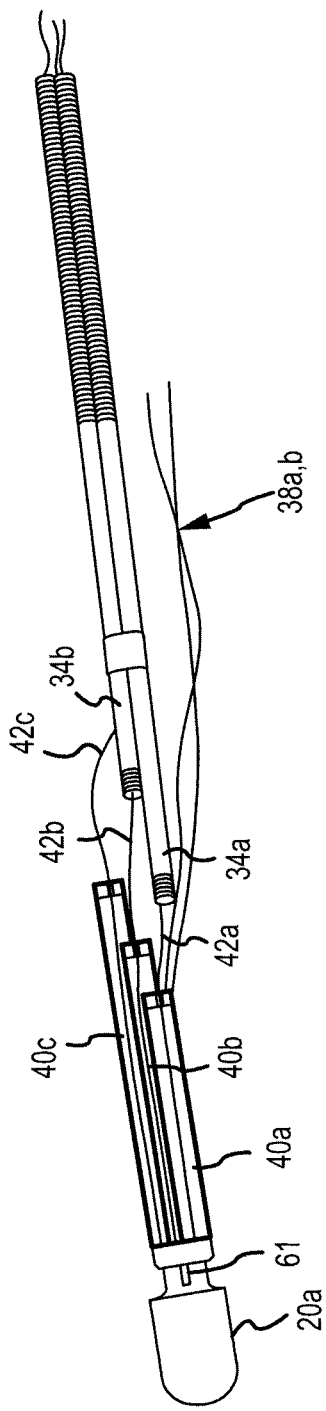
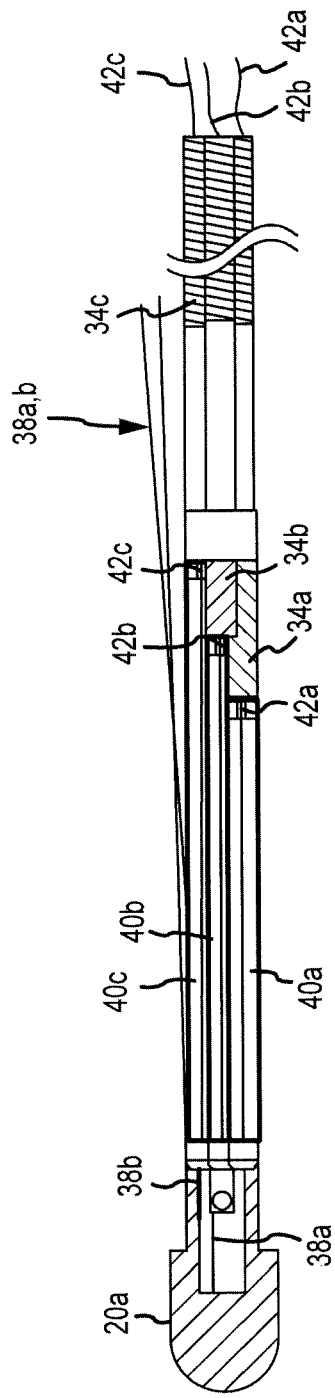
FIG. 16
FIG. 17

TRI-CURVE ELONGATE MEDICAL DEVICE

BACKGROUND a. Technical Field

The instant disclosure relates to elongate medical devices, including steerable elongate medical devices.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like.

To increase the ability to move and navigate a catheter within a patient's body, steerable catheters have been designed. Steerable catheters are often manipulated by selectively tensioning one or more deflection wires running along the length of the catheter, typically offset from a central axis of the catheter, thereby deflecting the distal end of the steerable catheter in one or more directions or planes. These deflection wires are sometimes attached to a metallic catheter component located at the distal end of the catheter, such as one of the electrodes carried on the distal end of the catheter or a pull ring incorporated in the catheter. In other designs, the deflection wires are embedded in a portion of the distal end of the catheter or otherwise attached to the distal end.

Once the catheter has been positioned at the target site, it often becomes necessary for the catheter to assume a particular shape in order to perform its desired function (e.g., a particular curvature size or radius). Further, it may be desirable for a catheter to be capable of being deflected into multiple shapes.

One known multi-shape elongate medical device includes multiple pull rings, each attached to a different longitudinal portion of the catheter shaft. Each pull ring may be coupled to one or more deflection wires for movement in one or more planes. Examples of such a medical device are shown in U.S. patent application Ser. No. 12/347,100 (issued as U.S. Pat. No. 8,123,721) and U.S. patent application Ser. No. 13/406,152 (published as United States patent application publication no. US 2012/0203169 A1), both of which are hereby incorporated by reference in their entireties as though fully set forth herein.

The foregoing discussion is intended only to illustrate the present field and should not be taken as a disavowal of claim scope.

BRIEF SUMMARY

An embodiment of an elongate medical device may include a shaft body having a distal end portion and a proximal end portion and three or more deflection wire assemblies, each deflection wire assembly coupled to the distal end portion and configured to be deflected such that the distal end portion is deflected in substantially the same direction as each deflection wire assembly. Each deflection wire assembly may be configured such that the distal end portion deflects into a shape corresponding to each deflection wire assembly. In an embodiment, the respective shapes of the deflection wire assemblies define different deflection radii.

An embodiment of an elongate medical device may also comprise a shaft body having a distal end portion and a proximal end portion, a first deflection wire assembly comprising a first flat wire coupled to the distal end portion, the first deflection wire assembly configured to be deflected such that the distal end portion is deflected in a direction with a first radius of deflection, and a second deflection wire assembly comprising a second flat wire coupled to the distal end portion, the second deflection wire assembly configured to be deflected such that the distal end portion is deflected in substantially the same direction as the first deflection wire assembly with a second radius of deflection. The second radius of deflection may be smaller than the first radius of deflection.

An embodiment of an elongate medical device may also comprise a shaft body having a distal end portion and a proximal end portion and three or more deflection wire assemblies, each deflection wire assembly comprising a flat wire coupled to the distal end portion and configured to deflect the distal end portion. Each flat wire may have a respective length defining a respective deflection radius, wherein each deflection radius is different.

BRIEF DESCRIPTION OF THE DRAWINGS

FIG. 2 is a partial longitudinal cross-section of a distal end portion of the shaft of the medical device of FIG. 1.

FIGS. 3 and 4 are transverse cross-sectional views of the distal end portion of FIG. 2.

FIGS. 5 and 6 are plan views of an elongate medical device shaft in different stages of build-up.

FIG. 7 is a transverse cross-sectional view of a portion of the spring coil assembly of FIG. 6.

FIGS. 11-13 are plan views of an elongate medical device shaft in different stages of build-up.

FIG. 14 is a transverse cross-sectional view of the elongate medical device shaft of FIG. 13.

FIGS. 15-17 are plan views of an elongate medical device shaft in different stages of build-up.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
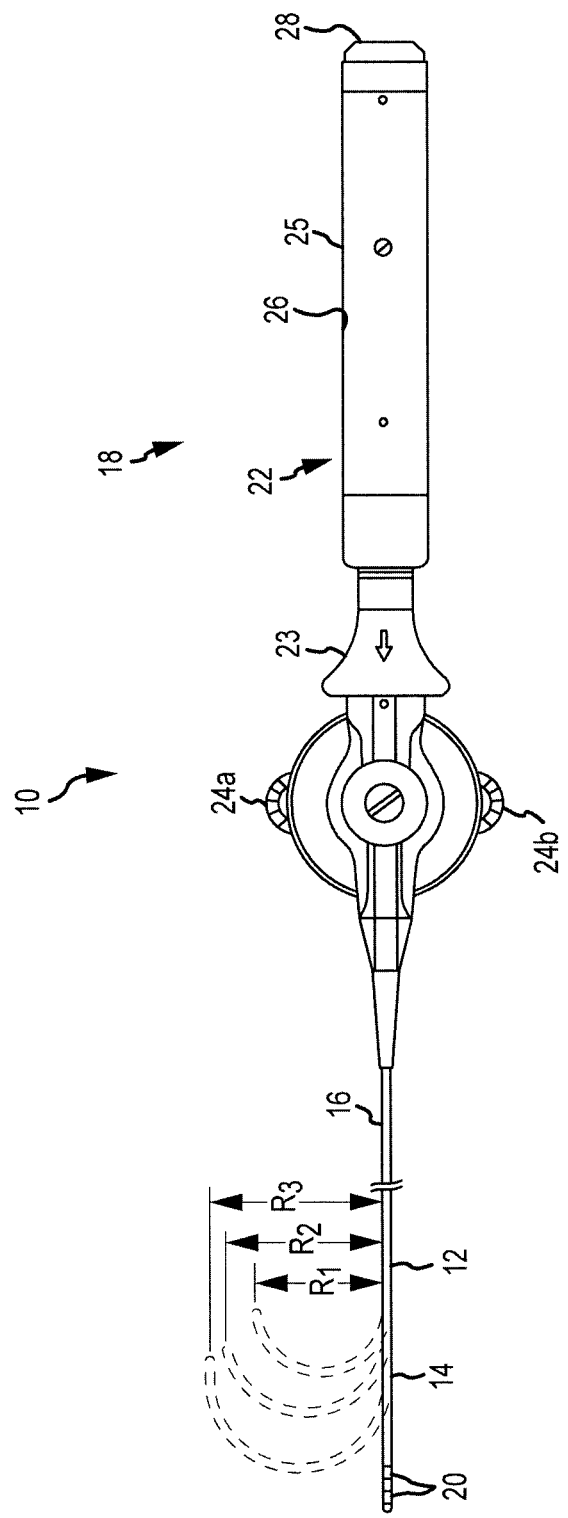
FIG. 1 is a plan view of an elongate medical device, with various deflection radii illustrated in phantom.

Referring now to the Figures, in which like reference numerals refer to the same or similar features in the various views, FIG. 1 is a plan view of an embodiment of an elongate medical device 10, with various deflection shapes (e.g., deflection radii) illustrated in phantom. The medical device 10 may find use in a number of medical procedures, including diagnostic procedures such as geometry collection and electrophysiology (EP) mapping, and therapeutic procedures such as ablation, for example only. Accordingly, the medical device 10 may include a number of features for navigation through the body of a patient as well as for diagnosis and/or therapy. The medical device will be referred to as a catheter 10 for ease of description, but it should be understood that the medical device may also be an introducer, guidewire, or other elongate medical device.

The catheter 10 may comprise a shaft 12 having a distal end portion 14 and a proximal end portion 16 and a handle assembly 18 coupled to the proximal end portion 16 of the shaft 12. The shaft 12 may be configured for selective deflection about a number of deflection radii. Though illustrated with three deflection radii $R_1$, $R_2$, $R_3$, the shaft may have more or fewer than three deflection radii. In an embodiment, two or more deflection radii may be in the same plane or direction (i.e., "up" in the plane of the page in the illustrated embodiment). In other embodiments, the deflection radii $R_1$, $R_2$, $R_3$ may be in different planes or directions. The shaft 12 will be described with reference to an embodiment with three deflection radii in the same direction, but it should be understood that the shaft 12 is not so limited.

The shaft 12 (e.g., the distal end portion 14) may include a number of sensors 20 for, e.g., ablation energy delivery, EP data collection, and/or position and orientation detection. The sensors 20 may include electrodes such as band electrodes, for example. The shaft 12 may additionally or alternatively include a tip electrode, coil sensors, temperature sensors, and other sensors known in the art. For fluid delivery, removal, and circulation, the shaft may also include one or more fluid lumens, ports, manifolds, and the like.

The handle assembly 18 may include a number of features to enable a user (e.g., a physician) to navigate the distal end portion 14 of the shaft 12 to an intended location within a patient's body. In an embodiment, the handle assembly 18 may include a linear actuation mechanism 22, two rotational actuation mechanisms 24a, 24b, a grip portion 26, and a connector 28. In an embodiment, the linear actuation mechanism 22 may include a fixed portion 23 and a sliding portion 25.

The linear actuation mechanism 22 and rotational actuation mechanisms 24a, 24b may be configured for manipulation by a user to selectively deflect the distal end portion 14 of the shaft 12. In an embodiment, each actuation mechanism 22, 24a, 24b may be configured to allow the user to deflect the distal end portion 14 along a different deflection radius. In an embodiment, the linear actuation mechanism 22 may be configured to allow the user to deflect the distal end portion 14 along the smallest deflection radius $R_1$, and the rotational actuation mechanisms 24a, 24b may be configured to allow the user to deflect the distal end portion along the intermediate and largest deflection radii $R_2$, $R_3$.

The rotational actuation mechanisms 24a, 24b may be configured for opposing use—i.e., rotation of a first rotational actuation mechanism 24a to deflect the distal end portion 14 of the catheter shaft 12 prevents deflection of the catheter shaft 12 using a second rotational actuation mechanism 24b, and vice-versa. In other embodiments, the rotational actuation mechanisms 24a, 24b may not be opposed.

The connector 28 may provide an electrical, mechanical, and/or fluid connection between elements in the shaft and handle assembly and external systems. For example, the connector 28 may provide a connection between the electrical leads of the electrodes 20 and an external ablation generator and/or mapping and navigation system. The connector 28 may also allow one or more fluid lumens extending through the shaft 12 and handle assembly 18 to be fluidly coupled with a source or destination of fluids, such as a pump or gravity feed for irrigation fluid, for example only.

As noted above, the catheter 10 may operate with a variety of external systems such as visualization systems, mapping systems, and navigation support and positioning systems (i.e., for determining a position and orientation (P&O) of a portion of the catheter). For example, the catheter 10 may be used with an EnSite™ Velocity™ system running a version of EnSite™ NavX™ software commercially available from St. Jude Medical, Inc., of St. Paul, Minn. and as also seen generally by reference to U.S. patent application Ser. No. 10/819,027 (issued as U.S. Pat. No. 7,263,397), hereby incorporated by reference in its entirety as though fully set forth herein. These exemplary systems with which the catheter 10 may be utilized can comprise conventional apparatus known generally in the art, for example, the EnSite™ Velocity™ system described above or other known technologies for locating/navigating a catheter in space (and for visualization), including for example, the Carto™ visualization and location system available from Biosense Webster, Inc., (e.g., as exemplified by U.S. patent application Ser. No. 08/793,371 (issued as U.S. Pat. No. 6,690,963) hereby incorporated by reference in its entirety as though fully set forth herein), the Aurora™ system available from Northern Digital Inc., a magnetic field based localization system such as that based on the MediGuide™ Technology available from St. Jude Medical, Inc. (e.g., as exemplified by U.S. patent application Ser. No. 09/782,528 (issued as U.S. Pat. No. 7,386,339); U.S. patent application Ser. No. 10/873,409 (issued as U.S. Pat. No. 7,197,354) and U.S. patent application Ser. No. 09/314,474 (issued as U.S. Pat. No. 6,233,476), all of which are hereby incorporated by reference in their entireties as though fully set forth herein) or a hybrid magnetic field-impedance based system, such as the Carto™ 3 visualization and location system available from Biosense Webster, Inc. (e.g., as exemplified by U.S. patent application Ser. No. 12/425,778 (issued as U.S. Pat. No. 7,848,789), which is hereby incorporated by reference in its entirety as though fully set forth herein). Some localization, navigation and/or visualization systems may involve providing a sensor for producing signals indicative of catheter location and/or distal portion orientation information, and can include, for example, one or more electrodes in the case of an impedance-based localization system such as the EnSite™ Velocity™ system running EnSite™ NavX™ software, which electrodes can already exist in some instances, or alternatively, one or more coils (i.e., wire windings) configured to detect one or more characteristics of a low-strength magnetic field, for example, in the case of a magnetic-field based localization system such as one including the MediGuide™ Technology described above.

FIG. 2 is a cross-sectional view of an exemplary embodiment of the distal end portion 14 of the shaft 12. The distal end portion 14 may include a body 30, a tip electrode 20a, a number of band electrodes 20b, 20c, 20d (which may be referred to collectively as the electrodes 20 or individually as an electrode 20), three deflection wire assemblies 32a, 32b, 32c (which may be referred to collectively as the deflection wire assemblies 32 or individually as a deflection wire assembly 32), three spring coil assemblies 34a, 34b, 34c (which may be referred to collectively as the spring coil assemblies 34 or individually as a spring coil assembly 34), and one or more thermocouples 38a, 38b (which may be referred to collectively as thermocouples 38 or individually as a thermocouple 38). The distal end portion 14 may extend along an axis A.

The body 30 may comprise melt-processing polymers and other materials, as known in the art, and may include a length, diameter, durometer (i.e., stiffness), and other properties appropriate for a desired function of the shaft 14. The body 30 may be manufactured according to known processes, in an embodiment.

The tip electrode 20a and band electrodes 20b, 20c, 20d may be provided for a number of purposes. For example, the electrodes 20 may be used to deliver ablation energy to a target site, to collect EP data, to function with a navigation system to determine the position and orientation of the distal end portion 14 of the shaft 12, and other purposes known in the art. Leads from the electrodes 20 may extend proximally as part of the electrical connection bundle 36, along with leads for the thermocouples 38a, 38b (see FIGS. 3 and 4). In embodiments including additional sensors or electrical elements, the electrical connection bundle 36 may include leads for such other electrical elements.

The thermocouples 38 that may be used, for example only and without limitation, for monitoring the temperature of the tip electrode 20a. In the embodiment shown, a first thermocouple 38a is coupled to the center of the tip electrode 20a and a second thermocouple 38b is coupled to the side of a stem portion of the tip electrode 20a. Of course, other thermocouple arrangements may be used.

The deflection wire assemblies 32 may be configured to, as noted above, be deflected such that the distal end portion 14 of the shaft 12 deflects. In an embodiment, the deflection wire assembly 32 may be placed in tension by a user of the catheter 10 to deflect the catheter shaft 12 along a particular arc, as described below.

Each deflection wire assembly 32 may be coupled to a respective spring coil assembly 34 (e.g., deflection wire assembly 32a to spring coil assembly 34a, deflection wire assembly 32b to spring coil assembly 34b, and deflection wire assembly 32c to spring coil assembly 34c). Each spring coil assembly 34 may provide structural support for the proximal end of a deflection wire assembly 32, as well as a passageway through which one or more elements of a deflection wire assembly 32 may extend.

FIGS. 3 and 4 are transverse cross-sections of the distal end portion 14, taken along lines 3-3 and 4-4 in FIG. 2, respectively. Referring to FIGS. 2-4, in an embodiment, each deflection wire assembly 32 may include a flatwire 40, an activation wire 42, and other elements to couple the flatwire 40 and activation wire 42 to each other and to the shaft 12, as described below. It should be noted that a reference to deflection wire assembly 32, flatwire 40, and activation wire 42 refer to one or more of the deflection wire assemblies 32a, 32b, 32c, flatwires 40a, 40b, 40c, and activation wires 42a, 42b, 42c shown in FIGS. 3 and 4 and throughout the drawings. Thus, the deflection wire assembly 32a may include a flatwire 40a and an activation wire 42a, the deflection wire assembly 32b may include a flatwire 40b and an activation wire 42b, and the deflection wire assembly 32c may include a flatwire 40c and an activation wire 42c. Along with a respective spring coil assembly 34, a respective flatwire 40 and activation wire 42 may cooperate to effect deflection of the distal end portion 14. The activation wire 42 may be placed in tension through the use of a deflection mechanism 22, 24a, 24b to deflect the distal end portion 14 along the arc effected by the flatwire 40 associated with that activation wire 42—i.e., tension of a first activation wire 42a effects deflection along an arc created by a first flatwire 40a, tension of a second activation wire 42b effects deflection along an arc created by a second flatwire 40b, and tension of a third activation wire 42c effects deflection along an arc created by a third flatwire 40c. Above and below, the flatwires 40a, 40b, 40c may be referred to collectively as the flatwires 40, or individually as a flatwire 40. Similarly, the activation wires 42a, 42b, 42c may be referred to above and below collectively as the activation wires 42 or individually as an activation wire 42. The arc (i.e., direction and radius) of deflection effected by a flatwire 40 may be defined by the shape, orientation, and/or length of the flatwire 40.

In an embodiment, the flatwires 40 may be arranged to partially overlap, as illustrated in FIG. 2. The overlap may be lateral—i.e., each flatwire 40 may have a length extending substantially parallel to the axis A of the distal end portion 14 and a lateral width substantially perpendicular to the axis A, and the lateral widths of the flatwires 40 may at least partially overlap. In particular, the flatwires 40 may be arranged so that the flatwire 40a effecting the smallest arc (i.e., the smallest deflection radius) may be placed on "top," the flatwire 40b effecting an intermediate deflection radius in the middle, and the flatwire 40c effecting the largest deflection radius on "bottom." For example, in the embodiment illustrated, the flatwires 40 may effect deflection out of the page, with the "top" flatwire 40a having the smallest deflection radius.

The deflection wire assemblies 32 may each be coupled to the distal end portion 14 of the shaft 12 at a junction 44. The junction 44 may also couple the deflection wire assemblies 32 to each other and/or to the tip electrode 20a, in an embodiment. The junction 44 may comprise solder or some other coupling mechanism or material known in the art.

With continued reference to FIGS. 2-4, each deflection wire assembly 32 may be coupled to a respective spring coil assembly 34. As illustrated in FIG. 4, both the flatwire 40 and the activation wire 42 may extend into a portion of the spring coil assembly 34. The spring coil assemblies 34 (and portions of deflection wire assemblies 32 extending therethrough) may be arranged in a triangular fashion. Where more or fewer deflection wire assemblies 32 and/or spring coil assemblies 34 are used (or in another three-coil and/or three-flatwire embodiment), another arrangement may be used. The flatwires 40 and activation wires 42 may be free to move proximally and distally within the spring coil assemblies 34. The spring coil assemblies 34, however, may be joined within a tube 46 over a portion of the respective lengths of the spring coil assemblies 34 and be bonded with, for example, a resin adhesive. The tube may comprise polyimide, in an embodiment, or another appropriate polymer or material known in the art.

As shown in FIG. 3, more proximally, the flatwires 40 have terminated, but the activation wires 42 continue to extend proximally through respective spring coil assemblies 34. The activation wires 42 may extend proximally to the handle 18 (shown in FIGS. 1 and 15) for coupling with a mechanism to deflect the distal end portion 14 of the shaft 12. The electrical connection bundle 36 and thermocouples 38 may likewise extend proximally through the shaft 12 to the handle 18.

Figure 5:
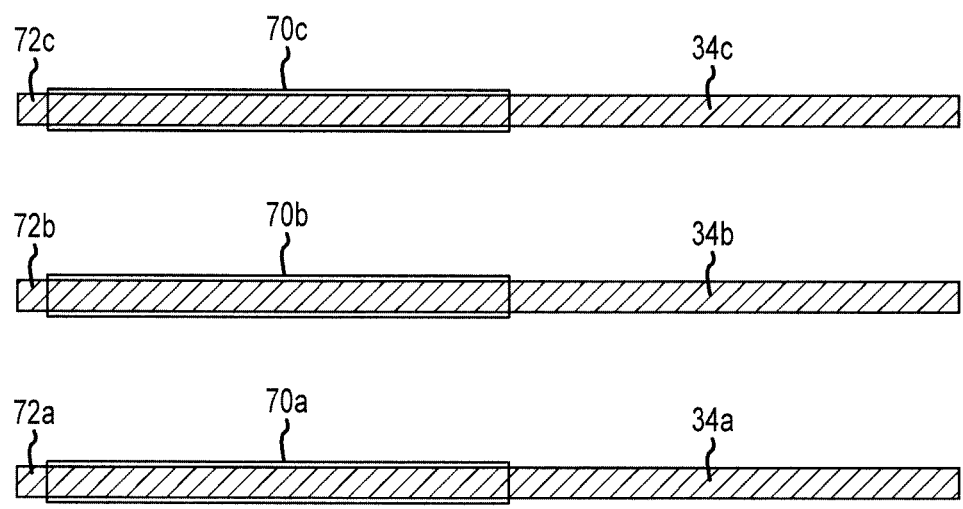

FIGS. 5-18 illustrate various stages in a method of manufacturing the distal end portion 14 to implement multiple deflection radii. The discussion will be with respect to an embodiment including three deflection radii, but it will be understood that a similar process may be used to manufacture an embodiment of a shaft having more or fewer than 3 deflection radii, or a shaft having 3 deflection radii that is otherwise different from the exemplary shaft 12 illustrated herein. FIGS. 5-7 illustrate various stages in a method of manufacturing the spring coil assemblies 34. In a first step, shown in FIG. 5, three spring coils 34a, 34b, 34c, of different lengths may each be partially covered in a respective tube 70a, 70b, 70c. Each tube 70a, 70b, 70c may comprise polyimide, in an embodiment, or another appropriate polymer or material known in the art. Each spring coil 34a, 34b, 34c may have a respective distal-most portion 72a, 72b, 72c. The distal-most portion 72a, 72b, 72c of each spring coil 70a, 70b, 70c may remain uncovered by tubes 70a, 70b, 70c.

Each spring coil 34 may comprise materials and dimensions appropriate for a desired function. In an embodiment, the external diameter of a spring coil 34 may each be about twenty-five thousandths of an inch (0.025 in), and the internal diameter of the spring coil 34 may each be about seventeen thousandths of an inch (0.017 in).

As shown in FIGS. 6 and 7, in a second step, a portion of the spring coil 34a may be further covered and bonded with tubes 74a, 76a which may respectively be about four (4) and two (2) centimeters in length. A portion of the spring coil 34c may be further covered and bonded with a tube 76c which may be about two (2) millimeters in length. The spring coils 34a, 34b, 34c (partially covered by the tubes 70a, 70b, 70c, 74a, 76a, 76c) may be arranged in a triangular fashion and bonded within a tube 46 with an adhesive which may be, in an embodiment, a resin adhesive.

Figure 8:
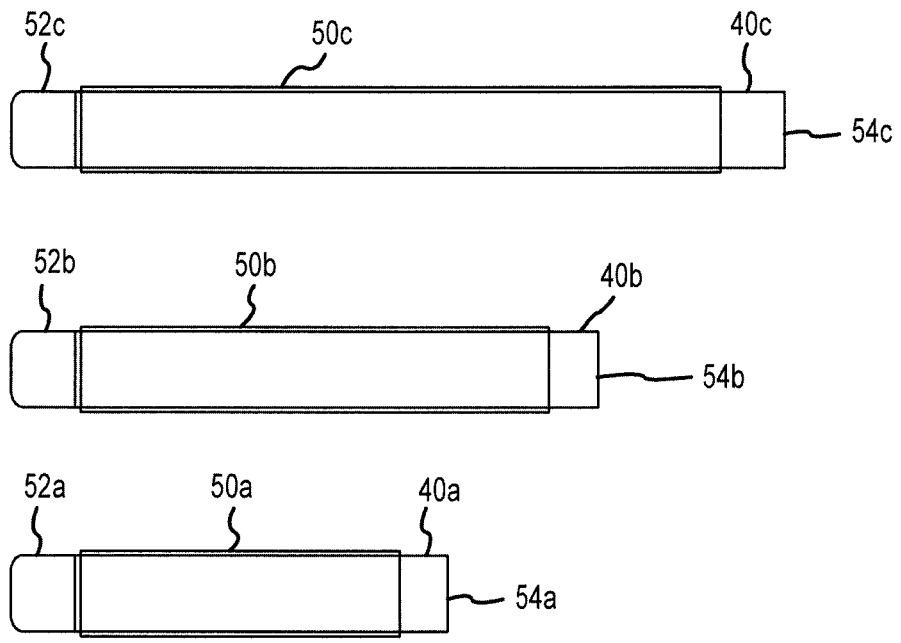
FIGS. 8 and 9 are plan views of an elongate medical device shaft in different stages of build-up.

FIGS. 8-15 illustrate various stages in a method of manufacturing and coupling the deflection wire assemblies 32. As shown in FIG. 8, three flatwires 40a, 40b, 40c (which, again, may be referred to collectively as flatwires 40 or individually as a flatwire 40) of different length may each be partially covered in a respective heat shrink tube 50a, 50b, 50c. Each flatwire 40a, 40b, 40c may have a respective proximal-most portion 54a, 54b, 54c and a respective distal-most portion 52a, 52b, 52c. Like the flatwires 40, the proximal-most portions 54a, 54b, 54c may be referred to collectively as the proximal-most portions 54 or individually as a proximal-most portion 54, and the distal-most portions 52a, 52b, 52c may be referred to collectively as the distal-most portions 52 or individually as a distal-most portion 52. The distal-most portion 52 and proximal-most portion 54 of each flatwire 40 may remain uncovered by the heat shrink 50a, 50b, 50c. The distal-most portion 52 of each flatwire 40 may be abraded to improve coupling with solder or other junction in a later step of manufacturing.

The flatwires 40 may comprise materials and dimensions appropriate for a desired function. In an embodiment, the flatwires 40 may each be between about five (5) and ten (10) centimeters in length with widths and thicknesses on the order of a few hundredths or thousandths of centimeters.

Figure 9:
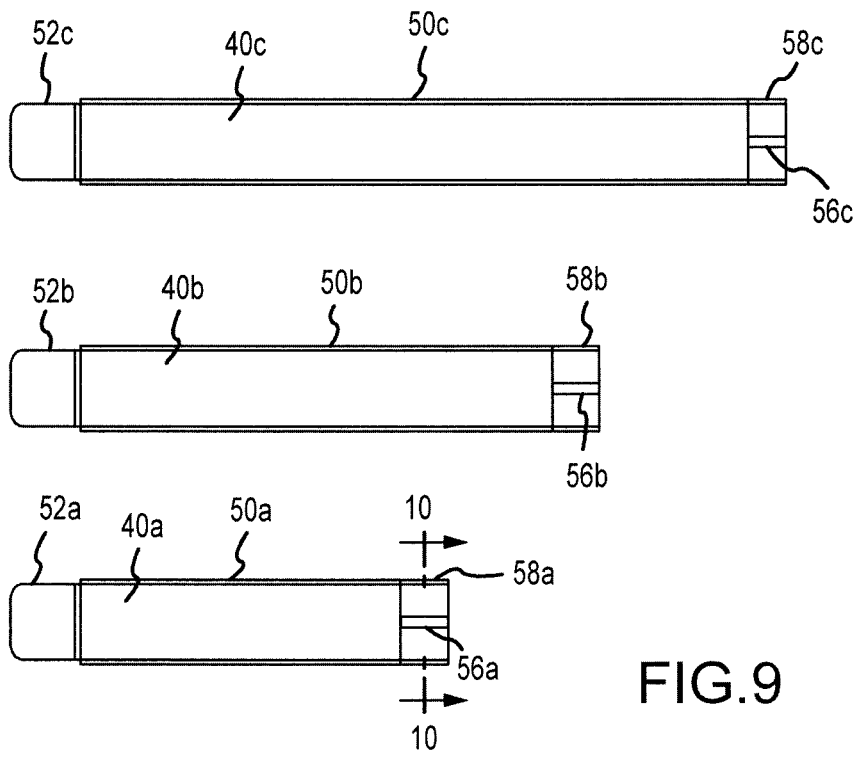
Figure 10:
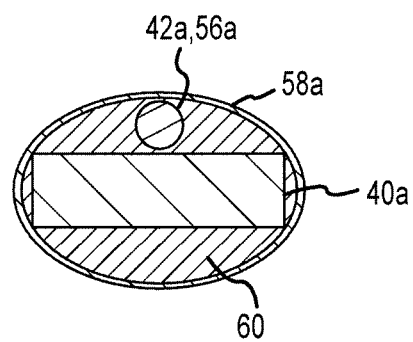
FIG. 10 is a transverse cross-sectional view of a portion of the deflection wire assembly of FIG. 8, with an activation wire added.

As shown in FIGS. 9 and 10, activation wire guide tubes 56a, 56b, 56c, in which the activation wires 42a, 42b, 42c may respectively be disposed, may be placed in separate bonding tubes 58a, 58, 58c. The proximal-most portions 54 of the flatwires 40 may also be placed in respective bonding tubes 58a, 58b, 58c, and the bonding tubes 58a, 58b, 58c filled with an adhesive 60 to couple each flatwire 40, each activation wire guide tube 56a, 56b, 56c, and each activation wire 42 within a respective bonding tube 58a, 58b, 58c. Because the activation wires 42a, 42b, 42c are within respective activation wire guide tubes 56a, 56b, 56c, the activation wires 42 may maintain the ability to slide distally and proximally relative to the bonding tubes 58a, 58b, 58c and the adhesive 60. The adhesive 60 may be, in an embodiment, resin.

Figure 11:
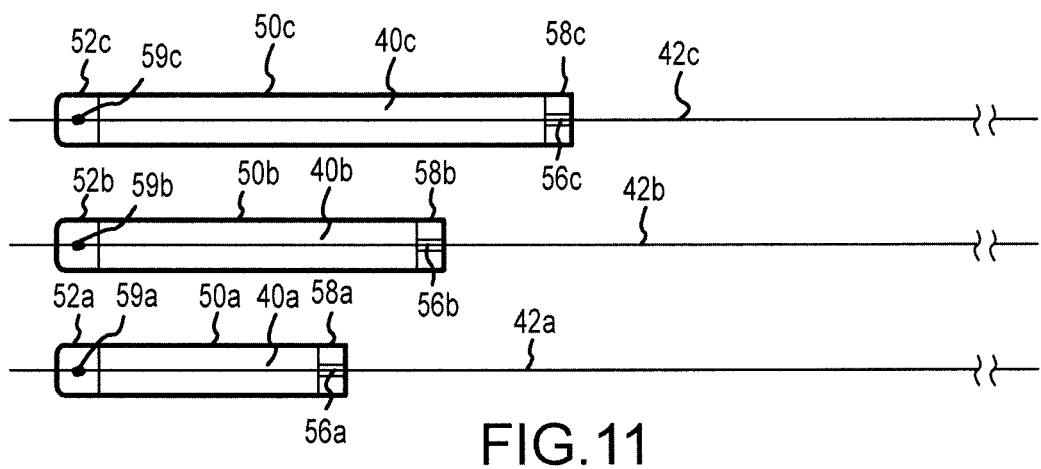
Figure 12:
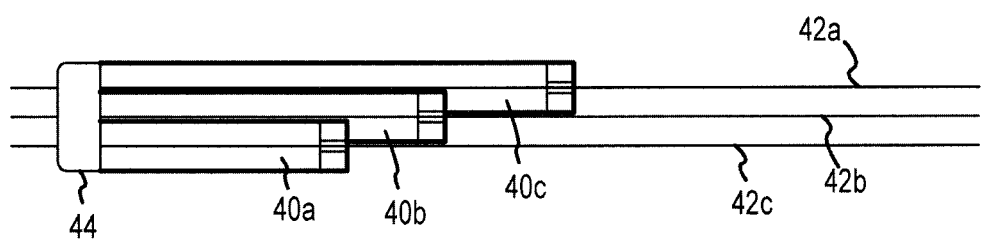

The activation wires 42 may be extended through respective activation wire guide tubes 56a, 56b, 56c and over the lengths of the flatwires 40, as shown in FIGS. 9-11 and be soldered at respective solder junctions 59a, 59b, 59c to respective distal-most portions 52 of the flatwires 40. The flatwires 40a, 4b, 40c may then be soldered together to form a junction 44 at their respective distal-most portions 52, as shown in FIG. 12. As a result of the solder junction 44, the deflection wire assemblies 32 may be coupled to substantially the same portion of the distal end portion 14 of the shaft 12 after manufacturing is completed. In another embodiment, the deflection wire assemblies 32 may be coupled to separate portions of the distal end portion 14.

After the flatwires 40 are soldered together, the tip electrode 20a may be coupled to the junction 44 with solder 61 and/or with adhesive, as shown in FIG. 13. As assembled, the flatwires 40 may be arranged to laterally overlap with the flatwire 40a associated with the smallest deflection radius on "top," as described above and as shown in further detail in FIGS. 13 and 14. Thermocouples 38a, 38b may then be coupled with the tip electrode 20a, as shown in FIG. 15.

With the deflection wire assemblies 32 coupled to each other and to the tip electrode 20a, and the spring coil assemblies 34 assembled, the flatwires 40 can then be coupled to respective spring coil assemblies 34, as shown in FIGS. 16 and 17. The activation wires 42 can be extended through respective spring coil assemblies 34, with thermocouple leads 38a, 38b remaining outside the spring coil assemblies 34. The entire assembly (excluding the distal portion of the tip electrode 20a) may then be inserted into and bonded to a prefabricated shaft body 30 to arrive at the construction shown in FIG. 2.

Figure 18:
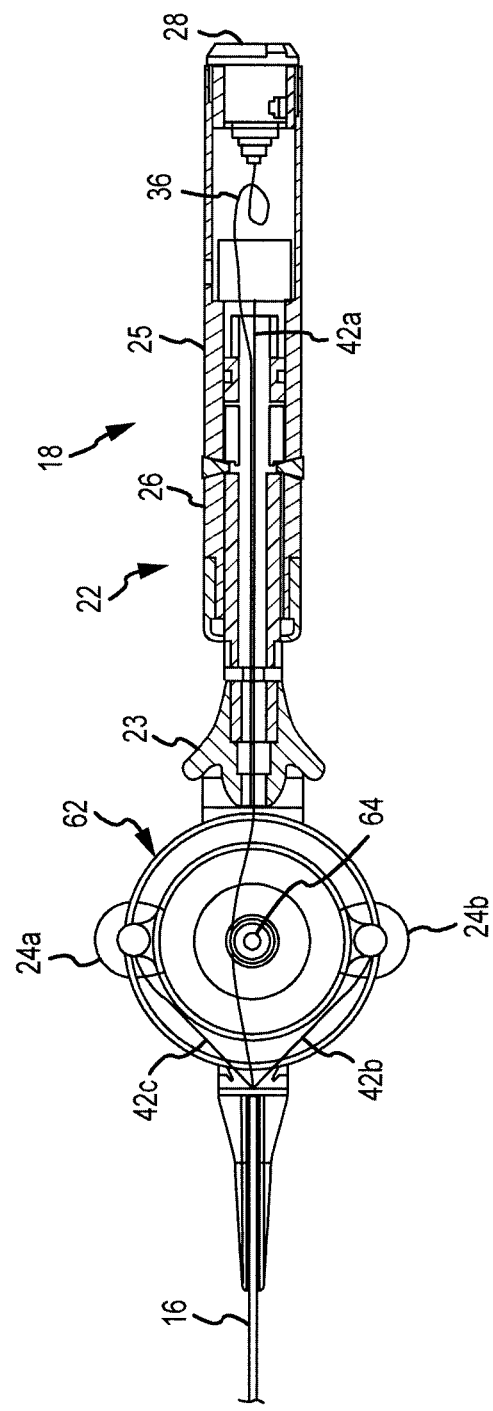
FIG. 18 is a partial cross-sectional view of the handle assembly of the elongate medical device of FIG. 1.

FIG. 18 is a cross-sectional view of a handle assembly 18 to which the proximal portion 16 of the completed shaft 12 may be coupled. The handle assembly 18 may include, as noted above, a linear actuation mechanism 22, two rotational actuation mechanisms 24a, 24b, a grip portion 26, and a connector 28. The connector 28 may be coupled with electrical connection bundle 36 and with thermocouple leads 38a, 38b.

In an embodiment and as shown in FIG. 18, the rotational actuation mechanisms 24a, 24b may each be coupled to or form a part of a single rotatable body 62 configured to rotate about a pivot 64. The third activation wire 42c (coupled to the largest-radius flatwire 40c) may be coupled to the first rotational actuation mechanism 24a. The second activation wire 42b (coupled to the intermediate-radius flatwire 40b) may be coupled to the second rotational actuation mechanism 24b. The first activation wire 42a (coupled to the smallest-radius flatwire 40a) may be coupled to the linear actuation mechanism 22—i.e., to the sliding portion 25 thereof. Of course, in another embodiment, the activation wires 42 may be distributed among the deflection mechanisms 22, 24a, 24b in another arrangement.

To deflect the distal end portion 14 along the smallest deflection radius (i.e., radius $R_1$, see FIG. 1), the sliding portion 25 of the linear actuation mechanism 22 may be displaced relative to the fixed portion 23. In the illustrated embodiment, the sliding portion 25 may be moved proximally relative to the fixed portion 23 to place tension on the activation wire 42a. To deflect the distal end portion 14 along the intermediate deflection radius (i.e., radius $R_2$, see FIG. 1), the second rotational deflection mechanism 24b may be rotated proximally—i.e., the rotatable body 62 may be rotated counter-clockwise. To deflect the distal end portion 14 along the largest deflection radius (i.e., radius $R_3$, see FIG. 1), the first rotational deflection mechanism 24a may be rotated proximally—i.e., the rotatable body 62 may be rotated clockwise.

Although a number of embodiments have been described above with a certain degree of particularity, those skilled in the art could make numerous alterations to the disclosed embodiments without departing from the spirit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An elongate medical device comprising:
a shaft body comprising a distal end portion and a proximal end portion, wherein said shaft body has an axis from said proximal end portion to said distal end portion; and
three deflection wire assemblies, each deflection wire assembly coupled to said distal end portion of said shaft body and configured to be deflected such that said distal end portion of said shaft body is deflected in substantially the same direction relative to said axis as the deflection of each deflection wire assembly, wherein each deflection wire assembly comprises a flat wire, each flat wire having a distal end, wherein said distal ends of said flat wires are coupled to a common location of said distal end portion of said shaft body, further wherein each flat wire has a respective length that is different from each other flat wire, wherein the respective length of each flat wire defines a respective radius of deflection of the distal end portion of said shaft body, wherein each respective radius of deflection is different.

2. The elongate medical device of claim 1, further comprising a tip electrode coupled to said distal end portion of said shaft body.

3. The elongate medical device of claim 2, wherein said common location is proximate to said tip electrode.

4. The elongate medical device of claim 1, wherein said three or more flat wires are coupled to said common location with a single solder joint.

5. The elongate medical device of claim 1, further comprising a handle assembly coupled to said proximal end portion of said shaft body, said handle assembly comprising:
a first manual manipulation mechanism coupled to a first one of said three or more deflection wire assemblies and configured for a user to apply tension to said first one of said three or more deflection wire assemblies;
a second manipulation mechanism coupled to a second one of said three or more deflection wire assemblies and configured for a user to apply tension to said second one of said three or more deflection wire assemblies; and
a third manipulation mechanism coupled to a third one of said three or more deflection wire assemblies and configured for a user to apply tension to said third one of said three or more deflection wire assemblies.

6. The elongate medical device of claim 5, wherein at least one of said first, second, and third manipulation mechanisms is configured for linear movement by a user to apply tension to a deflection wire assembly, and at least one of said first, second, and third manipulation mechanisms is configured for rotational movement by a user to apply tension to a deflection wire assembly.

7. The elongate medical device of claim 6, wherein two of said first, second, and third manipulation mechanisms are configured for opposing rotational movement by a user to selectively apply tension to the two deflection wire assemblies to which said two manipulation mechanisms are coupled.

8. The elongate medical device of claim 1, wherein each deflection wire assembly further comprises an activation wire coupled to said flat wire, wherein said distal end portion of said shaft body is configured to deflect in said direction responsive to tension applied to said activation wire.

9. The elongate medical device of claim 8, wherein each flat wire has a respective length extending generally parallel to said axis and a lateral width, wherein said flat wires at least partially laterally overlap.

10. The elongate medical device of claim 8, further comprising:
three or more spring coil assemblies, each spring coil assembly coupled to a respective one of the three or more deflection wire assemblies, wherein a respective activation wire extends through a respective spring coil assembly.

11. The elongate medical device of claim 10, wherein each spring coil assembly has a different respective length.

12. An elongate medical device comprising:
a shaft body having a distal end portion and a proximal end portion, wherein said shaft body has an axis from said proximal end portion to said distal end portion;
a first deflection wire assembly comprising a first flat wire coupled to said distal end portion and a first activation wire coupled to said first flat wire, said first deflection wire assembly configured to be deflected such that said distal end portion is deflected in a direction from said axis of said shaft body with a first radius of deflection, said first activation wire having a length that is greater than a length of said first flat wire; and a second deflection wire assembly comprising a second flat wire coupled to said distal end portion and a second activation wire coupled to said second flat wire, said second deflection wire assembly configured to be deflected such that said distal end portion is deflected substantially in the same said direction from said axis of said shaft body with a second radius of deflection, said second activation wire having a length that is greater than a length of said second flat wire;

wherein said second radius of deflection is smaller than said first radius of deflection.

13. The elongate medical device of claim 12, further comprising a third deflection wire assembly coupled to said distal end portion and configured to deflect said distal end portion substantially in said direction with a third radius of deflection, wherein said third radius of deflection is smaller than said second radius of deflection.

* * * * *